(12) United States Patent
Cuppoletti

(10) Patent No.: US 7,829,185 B2
(45) Date of Patent: Nov. 9, 2010

(54) SELECTIVELY PERMEABLE FILM SUPPORTED MEMBRANE

(75) Inventor: John Cuppoletti, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 372 days.

(21) Appl. No.: 10/569,694

(22) PCT Filed: Aug. 26, 2004

(86) PCT No.: PCT/US2004/027688

§ 371 (c)(1), (2), (4) Date: Feb. 27, 2006

(87) PCT Pub. No.: WO2005/022136

PCT Pub. Date: Mar. 10, 2005

(65) Prior Publication Data

US 2007/0026217 A1    Feb. 1, 2007

(51) Int. Cl.
*B32B 3/26* (2006.01)
*C12Q 1/70* (2006.01)

(52) U.S. Cl. ........................................ 428/304.4; 435/5

(58) Field of Classification Search .............. 428/304.4; 435/5
See application file for complete search history.

(56) References Cited

U.S. PATENT DOCUMENTS 5,098,532 A * 3/1992 Thompson et al. .......... 205/351
5,234,566 A * 8/1993 Osman et al. .......... 204/403.06
6,673,596 B1 * 1/2004 Sayler et al. ............. 435/288.7

OTHER PUBLICATIONS

Pintschovius J., et al, Charge translocation by the Na+/K+ -ATPase investigated on solid supported membranes; cytoplasmic cation binding and release. Biophys J 76(2): 827-836, Feb. 1999.
Pintschovius J., et al, Translocation by the NA+/K+ -ATPase investigated on solid supported membranes: rapid solution exchange with a new technique. Biophys J. 76(2): 814-826, Feb. 1999.
Florin et al, Painted supported lipid membranes. Biophys J. 64:375-383, Feb. 1993.
Seifert K, et al, Charge transport by ion translocating membrane proteins on solid supported membranes. Biophys J. 64:384-391, Feb. 1993.
Bamberg E. et al., Electrogenic properties of the Na+, K+ -ATPase probed by preseady state and relaxation studies. J. Bioenergetics and Biomembranes 33(5):401-405, Oct. 2001.

* cited by examiner

*Primary Examiner*—Victor S Chang
(74) *Attorney, Agent, or Firm*—Dinsmore & Shohl LLP

(57) ABSTRACT

A selectively permeable film supported membrane comprises a selectively permeable film comprising at least one ionomer; a bilayer formed on the film; and at least one transport substance incorporated into the bilayer. Methods for forming a selectively permeable film supported membrane comprise the steps of forming a bilayer on a selectively permeable film comprising at least one ionomer and incorporating at least one transport substance into the bilayer. Fuel cells, toxins detectors and protective devices comprise a selectively permeable film supported membrane.

19 Claims, 1 Drawing Sheet

SELECTIVELY PERMEABLE FILM SUPPORTED MEMBRANE

Figure 1:
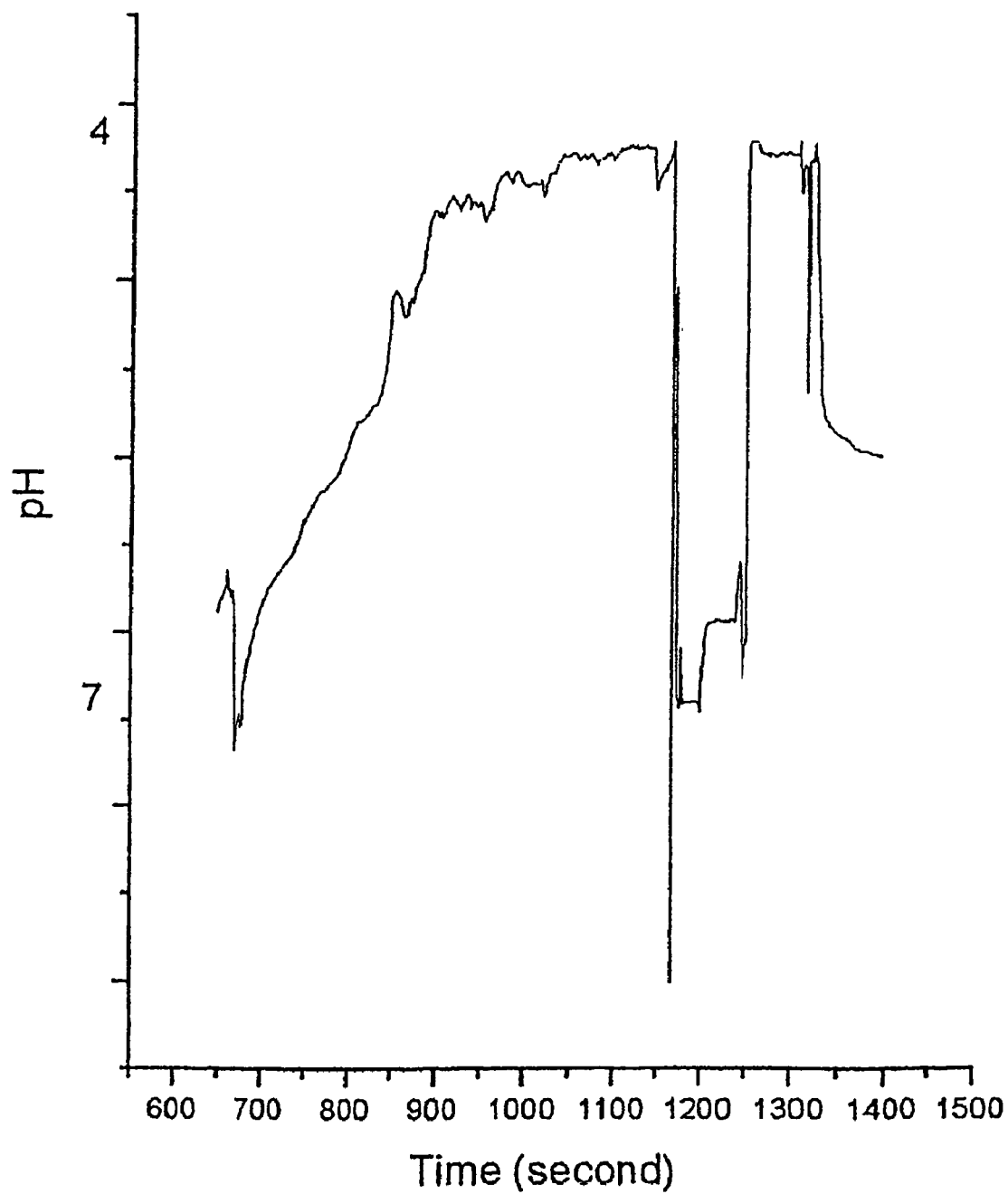

This invention was made, at least in part, with finds from the Federal Government, awarded through MURI grant number DAAD 19-0201-0227 ARMY. The U.S. Government therefore has certain acknowledged rights to the invention.

The present invention is directed toward a selectively permeable film supported membrane. The invention is also directed toward methods for forming a selectively permeable film supported membrane. Additionally, the invention is directed toward fuel cells, toxin detectors and protective devices comprising a selectively permeable film supported membrane.

Transport systems for utilizing energy have typically relied on membranes which could not selectively uptake, concentrate or release ions and/or molecules in an organized manner. Moreover, it would be advantageous to use selectively permeable flexible membrane technology to incorporate transport substances suitable for macroscopic and nanoscale preparations. Thus, there exists a substantial need for an improved membrane transport system that can selectively uptake, concentrate or release ions and/or molecules in an organized manner, and that can be used for macroscopic and/or nanoscale.

Accordingly, it is object of the invention to provide a novel selectively permeable membrane. It is a further object of the invention to provide methods for forming a selectively permeable membrane. It is yet a further object of the invention to provide devices comprising a selectively permeable membrane including, but not limited to, fuel cells, toxin detectors and protective devices against toxins.

In accordance with one aspect of the invention, a selectively permeable film supported membrane is provided. The membrane comprises a selectively permeable film comprising at least one ionomer; a bilayer formed on the film; and at least one transport substance incorporated into the bilayer.

In accordance with another aspect of the invention, there are provided methods for forming a selectively permeable film supported membrane. The methods comprise forming a bilayer on a selectively permeable film comprising at least one ionomer and incorporating at least one transport substance into the bilayer.

In accordance with yet another aspect of the invention, a fuel cell is provided. The fuel cell comprises a selectively permeable film comprising at least one ionomer; a bilayer formed on the film; and at least one transport substance incorporated into the bilayer. The transport substance is capable of generating an electrochemical gradient of protons.

In accordance with yet another aspect of the invention, a toxin detector is provided. The toxin detector comprises a selectively permeable film supported membrane and means to facilitate detection of a toxin in or near the membrane.

In accordance with yet another aspect of the invention, a protective device against toxins is provided. The protective device comprises a selectively permeable film supported membrane and a nonpermanent coating. The membrane is capable of generating an acid gradient. The coating protects against diffusion of toxins that are not degraded.

The present invention is advantageous for producing a selectively permeable film supported membrane that can utilize energy for the selective uptake, concentration, and/or release of ions and/or molecules in an organized manner. In addition, the selectively permeable film supported membrane is suitable for macroscopic and/or nanoscale preparations.

Additional embodiments, objects and advantages of the invention will become more fully apparent in view of the following detail description.

The following detailed description will be more fully understood in view of the drawing comprising FIG. 1 which is a graph depicting that a selectively permeable film supported membrane according to the invention exhibits active transport of HCl.

Transport substances in biological systems are organized in various structures, leading to different transport functions on various surfaces and intracellular membranes of cells. Organization of transport substances allows for utilization of energy, uptake and concentration of ions and/or molecules across and into cells, and utilization of cell structures needed for life processes. Transport substances mat be highly regulated. Under some physiological conditions, ion transport proteins capable of moving billions of ions per second can be reversibly silenced and again opened by intracellular regulators, thereby controlling the flow of solute. The exit and entry of ions and/or molecules across biological membranes control important life processes. Some of the most potent toxins (for example blowfish toxins that affect sodium channels, scorpion, snake and marine snail toxins and organophosphates) affect the transport substances and thus are highly toxic.

Transport substances are present in all living organisms. They are imbedded in lipid bilayer membranes that are otherwise essentially impermeable to water, to all inorganic ions, and only permeable to small hydrophobic substances, unless the lipid membranes also contain transport substances. Transport processes can be primary active (using energy of light or hydrolysis of high energy phosphate compounds, e.g.), secondary active (using gradients produced by primary active transport systems, e.g.), or passive, facilitating the diffusion of substances according to the concentration or electrical gradients. Transport substances are saturable and exhibit varying degrees of selectivity. In some cases, substrate selectivity can be broad and can be altered by changing the pore structures. Some transport substances such as sodium channels, are very selective for a single ion, while other transport substances such as the multiple drug resistance protein (MDR) which expels chemotherapeutics and other toxins from cells, are quite versatile in their transport specificity, and are capable of the transport of a number of compounds that are not structurally related. Such transporters, as they exist or after engineering, may be used to transport new materials in a specific manner.

Accordingly, the inventor has discovered a novel selectively permeable film supported membrane that can utilize energy for the selective uptake, concentration, and/or release of ions and/or molecules in an organized manner. In one embodiment, the present invention is directed to a novel selectively permeable film supported membrane. The membrane comprises a selectively permeable film comprising at least one ionomer; a bilayer formed on the film; and at least one transport substance incorporated into the bilayer. In a further embodiment, the present invention is also directed to methods for forming a selectively permeable film supported membrane. The methods comprise forming a bilayer on a selectively permeable film comprising at least one ionomer and incorporating at least one transport substance into the bilayer. The present invention is further directed to devices comprising the selectively permeable film supported membrane including, but not limited to, fuel cells, toxin detectors and protective devices against toxins.

The selectively permeable film supported membrane comprises a selectively permeable film. As used herein, "selectively permeable" is intended to refer to a film property which allows some ions and/or molecules to cross the film more easily than other ions and/or molecules. In one embodiment, the selectively permeable film supported membrane has an increased resistance to the flow of ions or molecules as compared to the selectively permeable film alone. In another embodiment, the film is selectively permeable to protons, water, or combinations thereof.

The selectively permeable film may be formed of any ionomer material which is selectively permeable, numerous examples of which are commercially available. As used herein "ionomer" is intended to refer to a polymer with a few groups that are ionisable. In one embodiment, the film is anionic. In another embodiment, the film is cationic. In yet another embodiment, the film contains a mixture of anions and cations. In one embodiment, the ionomer material comprises any porous material. In a further embodiment the ionomer material includes, but is not limited to, perfluorinated polymer, base polymer grafted with terminally sulfinated radicals, wherein the base polymer comprises substituted or unsubstituted polyolefin, substituted or unsubstituted vinyl polymer, or a copolymer thereof, or combinations thereof. In one specific embodiment, the film comprises Nafion®, available from Dupont, a perfluorinated polymer that contains small proportions of sulfonic or carboxylic ionic functional groups. Its general chemical structure can be seen below, where X is either a sulfonic or carboxylic functional group and M is either a metal cation in the neutralized form or an H+ in the acid form.

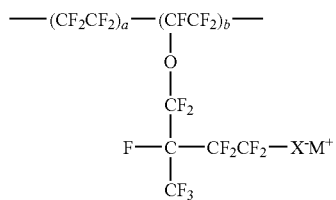

Structurally, Nafion® is complex with a unique equilibrium of ionic selectivities, as well as, ionic transport properties of perfluorinated ionomer membranes. This complex structure provides the ability to alter the original ionomer properties to specific uses and needs, such as, fuel cell operations.

The selectively permeable film supported membrane also comprises a bilayer formed on the film. As used herein, "bilayer" is intended to refer to at least two layers of a lipid. The layers include, but not limited to, a biological lipid, a synthetic lipid, or combinations thereof. In one embodiment, the bilayer is formed on one side of the film. In another embodiment, the bilayer is formed on both sides of the film.

The selectively permeable film supported membrane further comprises at least one transport substance incorporated into the bilayer. These transport substances can utilize energy for the selective uptake, concentration, and/or release of ions and/or molecules in an organized manner. As used herein, "transport substance" is intended to refer to a substance which permits the passage of certain ions and/or molecules, but not others, into the bilayer of the selectively permeable film supported membrane. The substance includes, but is not limited to, native protein, recombinant protein or combinations thereof. Surprisingly, the transport substance maintains transport function when it has been incorporated into the bilayer. In one embodiment, the bilayer formed on the selectively permeable film may be referred to as a macroscopic membrane, while the transport substance may be referred to as a nanostructure. In a further embodiment, the transport substances comprise vectorial transport function.

In accordance with the present invention, one skilled in the art would recognize the various methods suitable for incorporating at least one transport substance into the bilayer. In one embodiment, the transport substance may be spontaneously inserted into the bilayer. In another embodiment, the transport substance may be incorporated into the bilayer by a lipid vesicle, a detergent solution, or combinations thereof. The method of incorporating at least one transport substance into the bilayer may be fully or partially automated by robotics.

In one embodiment, the transport substance comprises the gastric HCl transport system which includes the gastric H/K ATPase, a K channel, and a Cl channel protein. The K Channel and Cl channel are regulated by changes in pH, voltage, and ion concentrations, and are under regulation by covalent modifiers. The HCl formed by these transport substance may be used as a general biocide for killing bacteria, fungi, and viruses, a physiologically relevant function of HCl in the digestive tract, and for inactivation of peptides, proteins, and acid sensitive organic compounds. Since each $H^+$ produced results in an equivalent of $OH^-$ from the splitting of water, production of base on the opposite side of the membrane provides equally useful chemical secretions. HCl may be used for the concentrative uptake of weak bases such as tributylamines (a stabilizer of sarin) to high levels for the purposes of detection of the toxin. In the case of weak bases such as tributyl amine, the unionized weak base passively crosses the lipid membrane, and becomes protonated. The protonated weak base accumulates, since the charged compound cannot cross the membrane. Similarly, weak acids such as dinitrophenol, picric acid and trinitrotoluene may be detected with such membranes based on their ability, acting as protonophores, to collapse HCl gradients.

Moreover, chemical and electrical gradients may be interconverted according to chemiosmotic hypothesis. Accumulation of any substance may be accomplished at the expense of a gradient, as long as an appropriate transport substance that recognizes the electrical or chemical gradient and the ion and/or molecule in question is available. Thus, HCl gradients may be used for the accumulation of another ion and/or molecule as long as another transport substance may be identified or engineered to respond to the electrical or chemical gradients in exchange for the ion and/or molecule in question.

In another embodiment, the transport substance may comprise ion channels and transporters involved in maintaining homeostasis. These transport substances include, but are not limited to, H, K, Na, $Ca^{2+}$ gradients. These gradients may be inter-converted by a variety of techniques, including, but not limited to, the use of synthetic and natural exchange ionophores such as nigericin (a K/H exchanger), monensin (a Na/H exchanger), ionomycin (a $Ca^{2+}$/H exchanger) or a combination of FCCP (an electrogenic protonophores) with an electrogenic ionophore such as valinomycin.

When HCl transport is successfully incorporated into a selectively permeable film supported membrane, it follows that Na, K, and $Ca^{2+}$ gradients may also be generated using other primary active transport substances. The HCl transport system is not unique in producing large gradients. A close relative of the H/K ATPase is the Na/K ATPase (64% amino acid homology). The Na/K ATPase accomplishes the electrogenic movement of 3 Na for 2 K. With other appropriate transporters, it can accomplish the production of charge and sodium gradients that can also be employed by other transport substances for the selective concentration (or release) of other ions and/or molecules. The Na/K ATPase is also available in large quantities and has been reconstituted into a variety of systems, including solid supported membranes. An example of sodium dependent secondary active transport proteins in nature include the sodium dependent glucose transporter that is responsible for the concentrative uptake of glucose from the intestine using the electrochemical gradient produced by the Na/K ATPase. Glucose transporters present on the basolateral membrane of the intestinal cell facilitate the downhill transport of glucose into the blood.

These and other transport substances, which are controlled by pH, ionic conditions, membrane voltage, and/or intracellular second messengers, may be genetically engineered to function in the environment of the membrane of the present invention when control elements are missing, or when the substance would react with environmental agents, using techniques within the ability of those of ordinary skill in the art, in view of the present disclosure.

The present invention is also directed toward methods for forming a selectively permeable film supported membrane. The methods comprise forming a bilayer on a selectively permeable film comprising at least one ionomer and incorporating at least one transport substance into the bilayer. The step of forming a bilayer on a selectively permeable film comprises the steps of: forming a lipid monolayer; contacting a selectively permeable film with the lipid monolayer a first time; and contacting the selectively permeable film a second time with the lipid monolayer, thereby forming a bilayer on the selectively permeable film.

As used herein, "lipid monolayer" is intended to refer to a single lipid layer. The lipid layer includes, but is not limited to, a biological lipid, a synthetic lipid, or combinations thereof. One skilled in the art will appreciate the various known techniques for forming a lipid monolayer, any of which may be used herein. In one embodiment, the lipid monolayer is formed in an aqueous solution of a Langmuir-Blodget (L-B) device. Thus, in a specific embodiment, the bilayer may be formed by dipping a selectively permeable film through a lipid monolayer in an L-B device to form a first layer, and then removing the film with the first layer thereon through the monolayer and out of the L-B device to form the second layer. In another embodiment, the bilayer is formed on one side of the film. In another embodiment, the bilayer is formed on both sides of the film.

The present invention is also directed toward a fuel cell. The fuel cell comprises a selectively permeable film comprising at least one ionomer, a bilayer formed on the film and at least one transport substance incorporated into the bilayer. The transport substance is capable of generating an electrochemical gradient of protons. In one embodiment, the electrochemical gradient of protons is continuous. In a further embodiment, the electrochemical gradient of protons is produced at ambient temperatures. In a more specific embodiment, a continuous production of hydrogen ions is obtained and serves as a primary source of protons for a fuel cell.

The present invention is further directed toward toxin detectors. A toxin detector according to the invention comprises a selectively permeable film supported membrane and means to facilitate detection of a toxin in or near the membrane. One skilled in the art will appreciate the various means for detecting a toxin in or near the membrane, which are known in the art and suitable for use herein. In one embodiment, the means to facilitate detection of a toxin includes, but is not limited to, antibodies, peptides, enzymes, or combinations thereof that can recognize molecular elements of an ion and/or molecule. In another embodiment, molecularly imprinted polymers may be used as a means to facilitate detection of a toxin. In yet another embodiment, transport substances may be modified in accordance with a particular ion and/or molecule, for example, an organophosphate. Other techniques to facilitate detection of a toxin include, but are not limited to, molecular imprinting, sensitized lanthanide luminescence, and membrane bound acetyl cholinesterase.

The invention is further directed toward protective devices against toxins. The device comprises a selectively permeable film supported membrane and a nonpermanent coating. The membrane is capable of generating an acid gradient. The nonpermanent coating protects against diffusion of toxins that are not degraded. One skilled in the art will appreciate the various nonpermanent materials to be protected that may be employed in the protective device, which are known in the art and suitable for use herein. In one embodiment, the material may be a surface of a living or non-living object. In one embodiment, the material to be protected is a fabric, such as clothing. In another embodiment, the material to be protected is a synthetic material. In yet a further embodiment, the material to be protected is a warfare-related article. The protective device may further comprise at least one catalyst facilitating transport. One skilled in the art will appreciate various catalysts which are known in the art for facilitating transport and suitable for use herein.

One skilled in the art will appreciate the various known chemical agents that may be released by activation of transport substances that respond to electrical/chemical gradients when appropriately constituted into a selectively permeable film supported membrane, in view of the present specification. In one embodiment, the chemical agent is an acid. In another embodiment, the chemical agent comprises glutathione, cysteine, S-330, or combinations thereof. Specifically, these chemical agents are known to protect cells against chemical warfare agents such as mustard gas and the like. Moreover, sodium-dependent and independent cysteine transporters and glutathione transporters suggest that a native or engineered protein (such as MDR variants or engineered channels) can facilitate the transport of S-330, or other substances, regardless of their chemical properties.

The membranes, methods and devices will be more fully understood in view of the examples.

EXAMPLE 1

This example demonstrates the formation of a bilayer on a selectively permeable film. A monolayer of phosphatidyl ethanolanine (Avanti Polar Lipids) is dissolved in hexane. The lipid monolayer is spread on a Langmuir-Blodget (LB) film device. Force is applied to form a monolayer on the LB device. A Nafion® film is attached, dipped down into the water, thereby contacting the monolayer a first time. The Nafion® film is then removed, contacting the monolayer a second time, thereby forming a bilayer.

The bilayer formed on the selectively permeable film is documented by a loss in surface area of the monolayer in the LB device. The calculated surface area of the monolayer closely approximates the calculated surface area required to form a bilayer on both sides of the Nafion® film.

EXAMPLE 2

This example demonstrates that a transport substance incorporated into a bilayer exhibits active transport of HCl. A one square inch sample of Nafion® membrane (112 mil thick) is washed in dilute buffered salt solution and then coated on one side with a bilayer of phosphatidyl ethanolamine using a Langmuir-Blodget film device. The bilayer coated side is then incubated with a suspension of H/K ATPase containing transport substances (approximately 50 µg) overnight at 10 degrees C.

The resultant bilayer and transport substance is then attached by an "O" ring to a plastic cup with an opening of 0.3 square cm (6.4 mm diameter). The bilayer and transport substance is oriented to the outside of the plastic cup, and the untreated side is oriented to the inside of the cup. The device is then washed in distilled water and 20 mM potassium-HEPES buffer, followed by distilled water. The plastic cup is then placed in a 1 ml solution of 20 mM potassium-HEPES buffer pH 7.0, and 20 mM potassium chloride. An adenosine triphosphate and magnesium chloride solution is prepared and adjusted to pH 7.0 with tris base. Adenosine triphosphate and magnesium chloride are then added at a final concentration of 1 mM each.

A pH electrode is placed in 1 ml distilled water with 20 mM potassium chloride in the plastic cup sealed at the bottom by the membrane assembly. The pH of the solution in the cup is then recorded. As shown in FIG. 1, the pH of the water in the plastic cup at the start of the experiment is approximately 7.0. Upon addition of 25 microgram of valinomycin to the lower chamber to increase potassium permeability (675 sec), the pH of the water in the cup becomes more acidic, reaching a plateau at approximately pH 4.0. At the end of the experiment (1150 sec), the response to a pH 7.0 standard solution is measured, and then the response to a pH 4.0 standard solution is measured (1250 sec). Finally, the pH of the lower solution is measured.

The specific embodiments in the examples described herein are illustrative in nature only and are not intended to be limiting of the claimed compositions and methods. Additional embodiments and variations within the scope of the claimed invention will be apparent to those of ordinary skill in the art in view of the present disclosure.

The invention claimed is:

1. A selectively permeable film supported membrane comprising:
   a. a selectively permeable film comprising at least one ionomer;
   b. a lipid bilayer formed on the film; and
   c. at least one transport substance selected from the group consisting of HCl transport system, H/K ATPase, Na/K ATPase, K/H exchanger, Na/H exchanger, and $Ca^{2+}$/H exchanger, incorporated into the lipid bilayer,
   wherein the at least one transport substance is capable of generating gradients selected from the group consisting of proton, potassium, sodium, chloride, and calcium ion gradients.

2. The membrane according to claim 1, wherein the selectively permeable film comprises: porous material; perfluorinated polymer; base polymer grafted with terminally sulphonated or carboxylated radicals, wherein the base polymer comprises substituted or unsubstituted polyolefin; substituted or unsubstituted vinyl polymer, or a copolymer thereof; or combinations thereof.

3. The membrane according to claim 1, wherein the lipid bilayer comprises biological lipid, synthetic lipid, or combinations thereof.

4. The membrane according to claim 1, wherein the selectively permeable film contains a positive charge.

5. The membrane according to claim 1, wherein the selectively permeable film contains a negative charge.

6. The membrane according to claim 1, wherein the selectively permeable film contains a mixture of positive and negative charges.

7. The membrane according to claim 1, wherein the transport substance is in a lipid vesicle, detergent solution or combinations thereof.

8. The membrane according to claim 1, wherein the transport substance comprises native protein, recombinant protein, or combinations thereof.

9. The membrane according to claim 1, wherein the transport substance maintains transport function.

10. The membrane according to claim 1, wherein the membrane has an increased resistance to the flow of ions or molecules as compared to the film alone.

11. A fuel cell, comprising:
    a. a selectively permeable film comprising at least one ionomer;
    b. a bilayer formed on the film; and
    c. at least one transport substance incorporated into the bilayer,
    wherein the transport substance is capable of generating an electrochemical gradient of protons.

12. The fuel cell according to claim 11, wherein the electrochemical gradient of protons is continuous.

13. The fuel cell according to claim 12, wherein the electrochemical gradient of protons is produced at ambient temperatures.

14. A toxin detector, comprising:
    a. a selectively permeable film supported membrane comprising:
       a selectively permeable film comprising at least one ionomer;
       a bilayer formed on the film; and
       at least one transport substance incorporated into the bilayer, wherein the transport substance is capable of transporting the toxin; and
    b. means to facilitate detection of a toxin in or near the membrane.

15. A protective device against toxins, comprising:
    a. a selectively permeable film supported membrane; and
    b. a material to be protected,
    wherein the membrane is capable of generating an acid gradient, and wherein the coating protects against diffusion of toxins that are not degraded.

16. The device according to claim 15, wherein the selectively permeable film supported membrane comprises:
    a. a selectively permeable film comprising at least one ionomer;
    b. a bilayer formed on the film; and
    c. at least one transport substance incorporated into the bilayer.

17. The device according to claim 15, wherein the material to be protected comprises a fabric, synthetic material, or combinations thereof.

18. The device according to claim 15, wherein the device further comprises at least one catalyst facilitating transport.

19. The device according to claim 15, wherein the protective device detoxifies toxins.

* * * * *